US010328040B2

(12) United States Patent
Marshall et al.

(10) Patent No.: US 10,328,040 B2
(45) Date of Patent: Jun. 25, 2019

(54) THERAPEUTIC METHODS

(71) Applicant: ARIZONA BOARD OF REGENTS ON BEHALF OF ARIZONA STATE UNIVERSITY, Scottsdale, AZ (US)

(72) Inventors: Pamela Marshall, Peoria, AZ (US); Peter Jurutka, Scottsdale, AZ (US); Carl Wagner, Glendale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/112,111

(22) PCT Filed: Jan. 20, 2015

(86) PCT No.: PCT/US2015/012066
§ 371 (c)(1),
(2) Date: Jul. 15, 2016

(87) PCT Pub. No.: WO2015/109318
PCT Pub. Date: Jul. 23, 2015

(65) Prior Publication Data
US 2016/0338981 A1    Nov. 24, 2016

Related U.S. Application Data

(60) Provisional application No. 61/928,890, filed on Jan. 17, 2014.

(51) Int. Cl.
| | | |
|---|---|---|
| A61K 31/192 | (2006.01) | |
| A61K 31/194 | (2006.01) | |
| A61K 31/44 | (2006.01) | |
| A61K 31/505 | (2006.01) | |
| A61K 31/69 | (2006.01) | |
| A61K 31/202 | (2006.01) | |
| A61K 31/235 | (2006.01) | |
| A61K 31/343 | (2006.01) | |
| A61K 31/357 | (2006.01) | |
| A61K 31/4418 | (2006.01) | |
| A61K 31/4965 | (2006.01) | |

(52) U.S. Cl.
CPC .......... *A61K 31/192* (2013.01); *A61K 31/194* (2013.01); *A61K 31/202* (2013.01); *A61K 31/235* (2013.01); *A61K 31/343* (2013.01); *A61K 31/357* (2013.01); *A61K 31/44* (2013.01); *A61K 31/4418* (2013.01); *A61K 31/4965* (2013.01); *A61K 31/505* (2013.01); *A61K 31/69* (2013.01)

(58) Field of Classification Search
CPC ............... A61K 31/192; A61K 31/194; A61K 31/202; A61K 31/235; A61K 31/343; A61K 31/357; A61K 31/44; A61K 31/4418; A61K 31/4965; A61K 31/505; A61K 31/69
See application file for complete search history.

(56) References Cited

U.S. PATENT DOCUMENTS

| | | | |
|---|---|---|---|
| 4,762,844 A | 8/1988 | Grohe et al. | |
| 4,826,984 A | 5/1989 | Berlin et al. | |
| 4,938,949 A | 7/1990 | Borch | |
| 4,980,509 A | 12/1990 | Maignan | |
| 5,006,550 A | 4/1991 | Chandraratna | |
| 5,587,367 A | 12/1996 | Reuchert | |
| 5,672,710 A | 9/1997 | Beard et al. | |
| 5,780,676 A | 7/1998 | Boehm et al. | |
| 5,962,731 A | 10/1999 | Boehm et al. | |
| 6,137,002 A | 10/2000 | Fisher | |
| 6,162,815 A | 12/2000 | Bernardon | |
| 6,172,112 B1 | 1/2001 | Brouillette et al. | |
| 6,291,677 B1 | 9/2001 | Vasudevan | |
| 6,303,785 B1 | 10/2001 | Vasudevan | |
| 6,313,107 B1 | 11/2001 | Vasudevan | |
| 6,545,049 B1 | 4/2003 | Canan-Koch et al. | |
| 7,655,699 B1 | 2/2010 | Boehm | |
| 8,101,662 B2 | 1/2012 | Chandraratna | |
| 8,389,538 B2 | 3/2013 | Kakuta et al. | |
| 8,460,576 B2 | 6/2013 | Kurisawa et al. | |
| 8,475,775 B1 | 7/2013 | Brouillette | |
| 9,193,672 B2 | 11/2015 | Yu | |
| 9,596,758 B2 | 3/2017 | Tatsuta | |
| 2003/0008273 A1* | 1/2003 | Perlmann | A61K 31/00 435/4 |
| 2003/0135053 A1 | 7/2003 | Bernardon | |

(Continued)

FOREIGN PATENT DOCUMENTS

| | | |
|---|---|---|
| EP | 0637297 B1 | 8/2000 |
| EP | 1180520 A1 | 2/2002 |

(Continued)

OTHER PUBLICATIONS

Adams, et al., "Discovery of GSK 1070916, a Potent and Selective Inhibitor of Aurora B/C Kinase", J. Med. Chem. 53: 3973-4001 (2010).

(Continued)

*Primary Examiner* — Yong S. Chong
(74) *Attorney, Agent, or Firm* — Viksnins Harris Padys Malen LLP

(57) ABSTRACT

The invention provides a method for a disease or condition associated with dopamine deficiency (e.g. depression, schizophrenia, or Parkinson's disease) in a mammal in need of such treatment comprising administering a compound that binds to RXR to the mammal.

16 Claims, 1 Drawing Sheet

(56) References Cited

U.S. PATENT DOCUMENTS

| | | |
|---|---|---|
| 2007/0129392 A1 | 6/2007 | Hong et al. |
| 2007/0185055 A1 | 8/2007 | Jiang et al. |
| 2010/0029689 A1 | 2/2010 | Hopper |
| 2010/0105728 A1 | 4/2010 | Lagu |
| 2010/0120742 A1 | 5/2010 | Kakuta et al. |
| 2010/0144821 A1 | 6/2010 | Carter et al. |
| 2016/0263189 A1* | 9/2016 | Burstein ............. A61K 38/185 |

FOREIGN PATENT DOCUMENTS

| | | |
|---|---|---|
| JP | 2014076953 A | 5/2014 |
| WO | 1993021146 A1 | 10/1993 |
| WO | 1998045242 A1 | 10/1998 |
| WO | 1999051562 A1 | 10/1999 |
| WO | 1999056740 A1 | 11/1999 |
| WO | 2000064260 A1 | 11/2000 |
| WO | 2002018361 A2 | 3/2002 |
| WO | 2002049632 A1 | 6/2002 |
| WO | 2004058762 A1 | 7/2004 |
| WO | 2005058803 A1 | 12/2004 |
| WO | 2005011573 A2 | 2/2005 |
| WO | 2005058301 A1 | 6/2005 |
| WO | 2005058798 A2 | 6/2005 |
| WO | 2006036394 A2 | 4/2006 |
| WO | 2007063681 A1 | 6/2007 |
| WO | 2008025965 A2 | 3/2008 |
| WO | 2008105386 A1 | 9/2008 |
| WO | 2010096264 A2 | 8/2010 |
| WO | 2011006157 A2 | 1/2011 |
| WO | 2011062017 A1 | 5/2011 |
| WO | 2011103321 A1 | 8/2011 |
| WO | 2013040227 A2 | 3/2013 |
| WO | 201356232 A2 | 4/2013 |
| WO | 2015130973 A1 | 9/2015 |

OTHER PUBLICATIONS

Altucci, et al., "RAR and RXR modulation in cancer and metabolic disease", Nature Rev. Drug Discovery vol. 6, 793-810, (2007).
Amoutzias, "A protein interaction atlas for thenuclear receptors: properties and quality of a hub-based dimerisationnetwork", BMC Syst. Biol. 1, 34, 12 pages (2007).
Assaf, "Minimizing adverse side-effects of oral bexarotene in cutaneous T-cell lymphoma: an expert opinion.", Br. J. Dermatol. 155, 261-266 (2006).
Atigadda, et al., "Conformationally Defined Retinoic Acid Analogues. 5. Large-Scale Synthesis and Mammary cancer Chemopreventive Activity for (2E,4E,6Z,8E)-8- (3',4'-Dihydro-1'(2'H)-naphthalen-1'-ylidene)-3,7-dimethyl-2,4,6-octatrienoic Acid (9cUAB30)", Journal of Medicinal Chemistry 46(17), 3766-3769 (2003).
Atigadda, et al., "Methyl substitution of a rexinoid agonist improves potency and reveals site of lipid toxicity", Journal of Medicinal Chemistry 57(12), 5370-5380 (2014).
Boehm, et al., "Design and Synthesis of Potent Retinoid X Receptor Selective Ligands That Induce Apoptosis in Leukemia Cells", Journal of Medicinal Chemistry 38, 3146-55 (1995).
Boehm, et al., "Synthesis and Structure-Activity Relationships of Novel Retinoid X Receptor-Selective Retinoids", Journal of Medicinal Chemistry 37, 2930-2941 (1994).
Carpentier, "The glucocorticoid receptor is a co-regulator of the orphan nuclear receptor Nurr1", J. Neurochem. 104, 777-789 (2008).
Cesario, et al., "Differentiation and growth inhibition mediated via the RXR:PPARgamma heterodimer in colon cancer", Cancer Letters 240(2), 225-233 (2006).
Chu, "Nurr1 in Parkinson's disease and relateddisorders", J. Comp. Neural. 494, 495-514 (2006).
Cramamer, et al., "ApoEdirected therapeutics rapidly clear β-amyloid and reverse deficits in AD mouse models", Science 335, 1503-1506 (2012).
Dai, et al., "Liver X receptor β protects dopaminergic neurons in a mouse model of Parkinson disease", Proc. Natl. Acad. Sci. U.S.A. 109, 13112-13117 (2012).

Daiss, et al., "Crystal Structure Analysis, and Pharmacological Characterization of Disila-bexarotene, a Disila-Analogue of the RXR-Selective Retinoid Agonist Bexarotene", Organometallics 24, 3192-3199 (2005).
Dawson, et al., "Conformational effects on retinoid receptor selectivity. 2. Effects of retinoid bridging group on retinoid X receptor activity and selectivity", J. Med. Chem. 38, 3368-3383 (1995).
Dimick, et al., "On the Meaning of Affinity: Cluster Glycoside Effects and Concanavalin A. J.", Am. Chem. Soc. 121, 10286-10296 (1999).
Dragnev, et al., "A Proof-of-Principle Clinical Trial of Bexarotene in Patients with Non-Small Cell Lung Cancer", Clin. Cancer Res. 13, 1794-1800 (2007).
Dubois, et al., "Identification of a potent agonist of the orphan nuclear receptor Nurr1", ChemMedChem 1, 955-958 (2006).
Duvic, et al., "BexaroteneWorldwide Study Group. Bexarotene is effective and safe for treatmentof refractory advanced-stage cutaneous T-cell lymphoma: multinationalphase II-III trial results", J. Clin. Oncol. 19, 2456-24571 (2001).
Egea, et al., "Molecular recognition of agonist ligands by RXRs", Mol. Endocrinol. 16, 987-997 (2002).
Esteva et al. "Multicenter Phase II Study of Oral Bexarotene for Patients With Metastatic Breast Cancer", Journal of Clinical Oncology 21(6), 999-1006 (2003).
Fantini, et al., "Bexarotene blocks calcium-permeable ion channels formed by neurotoxic Alzheimer's β-amyloid peptides.", ACS Chemical Neuroscience 5, 216-224 (2014).
Farmer, et al., "Aza-retinoids as novel retinoid X receptor-specific agonists", Bioorg. Med. Chem. Lett. 16, 2352-2356 (2006).
Faul, et al., "Synthesis of Novel Retinoid X Receptor-Selective Retinoids", J. Org. Chem. 66, 5772-5782 (2001).
Field, et al., "LXR/RXR ligand activation enhances basolateral efflux of beta-sitosterol in CaCo-2 cells", J. Lipid Res. 45, 905-913 (2004).
Forman, et al., "Unique response pathways are established by allosteric interactions among nuclear hormone receptors", Cell 81, 541-550 (1995).
Friling, et al., "Activation of Retinoid X Receptor increases dopamine cell survival in models for Parkinson's disease", BMC Neurosci. 10, 146-153 (2009).
Fujii, et al., "Metabolic inactivation of retinoic acid by a novel P450 differentially expressed in developing mouse embryos", The EMBO Journal 16, 4163-4173 (1997).
Fujii, et al., "Modification at the acidic domain of RXR agonists has little effect on permissive RXR-heterodimer activation", Bioorganic & Medicinal Chemistry Letters 20, 5139-5142 (2010).
Furmick, et al., "Modeling, synthesis and biological evaluation of potential retinoid X receptor-selective agonists: novel halogenated analogues of 4-[1-(3,5,5,8,8-pentamethyl-5,6,7,8-tetrahydro-2-naphthyl)ethynyl]benzoic acid (bexarotene)", ChemMedChem 7(9), 1551-1566 (2012).
Galleguillos, "Nurr1 regulates RET expression in dopamine neurons of adult ratmidbrain", J. Neurochem. 114, 1158-1167 (2010).
Gandi, "Reactions of Some Aromatic Nitro Compounds with Alkali Metal Amides", J. Org. Chem. 44(25), 4705-4707 (1979).
Garcia, et al., "Pyrazine arotinoids with inverse agonist activities on the retinoid and rexinoid receptors", Chembiochem 10, 1252-1259 (2009).
Gernert, et al., "Design and Synthesis of Fluorinated RXR Modulators", Bioorg. Met Chem. Lett. 13, 3191-3195 (2003).
Gorman, et al., "In vitro metabolic characterization, phenotyping, and kinetic studies of 9cUAB30, a retinoid X receptor-specific retinoid", Drug Metabolism & Disposition 35(7), 1157-1164 (2007).
Grenningloh, et al., "Cutting Edge: Inhibition of the Retinoid X Receptor (RXR) Blocks T Helper 2 Differentiation and Prevents Allergic Lung Inflammation", J. Immunol. 176, 5161-5166 (2006).
Grubbs, et al., "9cUAB30, an RXR specific retinoid, and/or tamoxifen in the prevention of methylnitrosourea-induced mammary cancers", Cancer Letters 201, 17-24 (2003).
Hansen, et al., "The low-toxicity 9-cis UAB30 novel retinoid down-regulates the DNA methyltransferases and has anti-telomerase activity in human breast cancer cells", International Journal of Oncology 30(3), 641-650 (2007).

(56) References Cited

OTHER PUBLICATIONS

Heller, et al., "Synthetic retinoids in dermatology", Canadian Medical Association Journal 10, 1129-1136 (1985).
Hermanson, et al., "Nurr1 regulates dopamine synthesis and storage in MN9Ddopamine cells", Exp. Cell Res. 288, 324-334 (2003).
Hintermann, et al., "Identification of a series of highly potent activators of the Nurr1 signaling pathway", Bioorg. Med. Chem. Lett. 17,193-196 (2007).
Jong, et al., "Conformational effects on retinoid recepetor selectivity. 1. Effect of 9-double bond geometry on retinoid X receptor activity", J. Med. Chem. 36, 2605-2613, (1993).
Jurutka, et al., "Modeling, synthesis, and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene) and (E)-3-(3-(1,2,3,4-tetrahydro-1,1,4,", Journal of Medicinal Chemistry 56, 8432-8454 (2013).
Kadkhodaei, et al., "Nurr1 is required formaintenance of maturing and adult midbrain dopamine neurons", J. Neurosci. 29, 15923-15932 (2009).
Kagechika, et al., "Retinobenzoic acids. 1. Structure-activity relationships of aromatic amides with retinoidal activity", J Med Chem 31, 2182-2192 (1988).
Kakuta, et al., "RXR Partial Agonist CBt-PMN Exerts Therapeutic Effects on Type 2 Diabetes without the Side Effects of RXR Full Agonists", ACS Medicinal Chemistry Letters 3, 427-432 (2012).
Kakuta, "Western-style Chinese (Kampo) medicine targeting retinoid X receptors (RXRs)", 248th ACS National Meeting, MEDI 102, San Francisco, CA. (2014).
Kapetanovic, et al., "Murine Oncogenicity and Pharmacokinetics Studies of 9-cis-UAB30, an RXR Agonist, for Breast Cancer Chemoprevention", International Journal of Toxicology 29(2), 157-164 (2010).
Keenan, et al., "Conformational Preferences in a Benzodiazepine Series of Potent Nonpeptide Fibrinogen Receptor Antagonists", J. Med. Chem. 42, 545-559, (1999).
Khuri, et al., "Multi-Institutional Phase I/II Trial of Oral Bexarotene in Combination With Cisplatin and Vinorelbine in Previously Untreated Patients With Advanced Non-Small-Cell Lung Cancer", Journal of Clinical Oncology 19, 2626-2637 (2001).
Rizvi, et al., "A Phase I study of LGD1069 in adults with advanced cancer", Clin. Cancer Res. 5, 1658-1664 (1999).
Sacchetti, et al., "Nurr1 enhances transcription of the human dopaminetransporter gene through a novel mechanism", J. Neurochem. 76,1565-1572 (2001).
Saijo, et al., "A Nurr1/CoREST pathway in microglia and astrocytes protects dopaminergicneurons from inflammation-induced death", Cell 137, 47-59 (2009).
Sakaki, et al., "Synthesis and Structure-activity Relationship of Nocel RXR antagonists: orally active antidiabetic and antiobesity agents", Bioorg. Med. Chem. Lett 17, 4804-4807 (2007).
Sakurada, et al., "Nurr1, an orphan nuclear receptor, is atranscriptional activator of endogenous tyrosine hydroxylase in neuralprogenitor cells derived from the adult brain", Development 126, 4017-4026 (1999).
Santin, et al., "Modulating Retinoid X Receptor with a Series of (E)-3-[4 Hydroxy-3-(3-alkoxy-5,5,8,8-tetramethyl-5,6,7,8-tetrahydronaphthalen-2-yl)phenyl]acrylic Acids and Their 4-Alkoxy Isomers", Journal of Medicinal Chemistry 52, 3150-3158 (2009).
Schimmel, et al., "4.5 kb of the rat tyrosine hydroxylase 5' flanking sequencedirects tissue specific expression during development and containsconsensus sites for multiple transcription factors", Mol. Brain Res. 74,1-14 (1999).
Schinelli, et al., "1-Methyl-4-phenyl-1,2,3,6-tetrahydropyridine metabolism and 1-methyl-4-phenylpyridinium uptake in dissociated cell cultures from the embryonic mesencephalon", J. Neurochem. 50(6), 1900-1907 (1988).
Sherman, et al., "Central hypothyroidism associated with retinoid X receptor-selective ligands", N. Engl. J. Med. 340 (14), 1075-1079 (1999).
Shibakura, et al., "Anticoagulant Effects of Synthetic Retinoids Mediated Via Different Receptors on Human Leukemia and Umbilical Vein Endothelial Cells", Blood 90(4), 1545-1551 (1997).
Sleiman, et al., "Characterisation of a novel NR4A2 mutation in Parkinson's diseasebrain", Neurosci. Lett. 457, 75-79 (2009).
Svensson, et al., "Crystal structure of the heterodimeric complex of LXRa and RXRb ligand-binding domains in a fully agonistic conformation", EMBO J. 22(18), 4625-4633 (2003).
Takahasi, et al., "2,5-Diaryl-1,3,2-dioxaborinanes: A New Series of Liquid Crystals", Bull. Chem. Soc. 62(12), 3896-3901 (1989).
Takamatsu, et al., "The First Potent Subtype-Selective Retinoid X Receptor (RXR) Agonist Possessing a 3-Isopropoxy-4-isopropylphenylamino Moiety, NEt-3IP (RXRalpha/beta-dual agonist)", ChemMedChem 3, 780-787 (2008).
Tan, et al., "Monitoring interactions between receptor tyrosine kinases and their downstream effector proteins in living cells using bioluminescence resonance energy transfer", Mol. Pharmacol. 72 (6), 1440-1446 (2007).
Thacher, et al., "Receptor Specificity of Retinoid-Induced Epidermal Hyperplasia: Effect of RXR-Selective Agonists and Correlation with Topical Irritation", Journal Pharmacology and Experimental Therapeutics 282(2), 528-534 (1997).
Thalesnano Nanotechnology Inc., "H-Cube Continuous-flow hydrogenation reactor", www.thalesnano.com/h-cube, Published: Apr. 9, 2006, Retrieved: Dec. 29, 2014.
Thompson, et al., "Distinct retinoid X receptor activation dunction-2 residues mediate transactivation in homodimeric and vitamin D receptor heterodimeric contexts", J. Mol. Endocrinol. 27(2), 211-227 (2001).
Traynelis, et al., "Ylide Methylation of Aromatic Nitro Compounds", J. Org. Chem. 31, 243-247 (1964).
Vahlquist, "What are Natural Retinoids", Dermatology 199(Suppl 1), 3-11 (1999).
Vuligonda, et al., "Enantioselective Synthesis of Potent Retinoid X Receptor Ligands: Differential Biological Activities of Individual Antipodes", J. Med. Chem. 44, 2298-2303 (2001).
Wagner, et al., "Modeling, synthesis and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid (bexarotene)", J. Med. Chem. 52, 5950-5966 (2009).
Wallen-MacKenzie, et al., "Nurr1-RXR heterodimers mediate RXR ligand-induced signaling in neuronal cells", Genes & Development 17, 3036-3047 (2003).
Wang, et al., "Structure and function ofNurr1 identifies a class of ligand-independent nuclear receptors", Nature 423, 555-560 (2003).
White, et al., "Identification of the retinoic acid-inducible all-trans-retinoic acid 4-hydroxylase", Journal of Biological Chemistry 271, 29922-29927 (1996).
Whitworth, et al., "The impact of novel retinoids in combination with platinum chemotherapy on ovarian cancer stem cells", Gynecologic Oncology 125, 226-230 (2012).
Winum, et al., "Synthesis of New Targretin® Analogues that Induce Apoptosis in Leukemia HL-60 Cells", Bioorg. Med. Chem. Lett. 12: 3529-3532 (2002).
Yamauchi, et al., "Inhibition of RXR and PPARgamma ameliorate diet-induced obesity and type 2 diabetes", J. Clin. Invest. 108, 1001-1013 (2001).
Yen, et al., "A Selective Retinoid X Receptor Agonist Bexarotene (Targretin) Prevents and Overcomes Acquired Paclitaxel (Taxol) Resistance in Human Non-Small Cell Lung Cancer.", British Journal of Cancer 94, 654-660 (2006).
Yen, et al., "Synergistic effect of a retinoid X receptor-selective ligand bexarotene (LGD1069, Targretin) and paclitaxel (Taxaol) in mammary carcinoma", Breast Cancer Res. Treat 88, 141-148 (2004).
Zetterstrom, et al., "Dopamine neuronagenesis in Nurr1-deficient mice", Science 276, 248-250 (1997).
Zhang, et al., "Induction of Apoptosis by Bexarotene in Cutaneous T-Cell Lymphoma Cells.", Clin Cancer Res 8, 1234-1240 (2002).
Zhang, et al., "Syntheses of isotopically labeled 4-[1-(3,5,5,8,8-pentamethyl-5,6,7,8-tetrahydro-2-naphthyl)ethenyl] benzoic acid

(56) References Cited

OTHER PUBLICATIONS (LGD1069), a potent retinoid x receptor-selective ligand", Journal of Labelled Compounds and Radiopharmaceuticals 36(7), 701-712 (1995).

Zimmermann, et al., "A yeast strain for simultaneous detection of mitotic crossing over, mitotic gene conversion, and reverse mutation", Mutat. Res. 28, 381-388, (1975).

Zimmermann, "Procedures used in the induction of mitotic recombination and mutation in the yeast *Saccharomyeces cerevisiae*", Mutat. Res. 31, 71-86 (1975).

Kiick, et al. "Incorporation of azides into recombinant proteins for chemoselective modification by the Staudinger ligation", Proc. Natl. Acad. Sci. U.S.A. 99(1), 19-24 (2002).

Koch, et al., "Identification of the First Retinoid X Receptor Homodimer Antagonist", J Med Chem 39(17), 3229-3234 (1996).

Koch, et al., "Synthesis of Retinoid X Receptor-Specific Ligands That Are Potent Inducers of Adipogenesis in 3T3-L1 Cells", Journal of Medicinal Chemistry 42, 742-750 (1999).

Kolesar, et al., "A pilot, first-in-human, pharmacokinetic study of 9cUAB30 in healthy volunteers", Cancer Prevention Research 3(12), 1565-1570 (2010).

La Vista-Picard, et al., "The receptor-DNA complex determines the retinoid response: a mechanism for the diversification of the ligand signal.", Molecular and Cellular Biology 16(8), 4137-4146 (1996).

Lagu, et al. "RXR-LXR heterodimer modulators for the potential treatment of dyslipidemia", Bioorganic & Medicinal Chemistry Letters 17, 3497-3503 (2007).

Le, "Decreased NURR1 gene expressionin patients with Parkinson's disease", J. Neurol. Sci. 273, 29-33 (2008).

Le, "Mutations in NR4A2 associated withfamilial Parkinson disease", Nat. Genet. 33, 85-89 (2003).

Lehmann, et al., "Retinoids selective for retinoid X receptor pathways", Science 258, 1944-1946 (1992).

Leid, et al., "Multiplicity Generates Diversity in the Retinoic Acid Signaling Pathways", Trends Biochem. Sci. 17, 427-433 (1992).

Lerner, et al. "Bexarotene as add-on to antipsychotic treatment in schizophrenia patients: a pilot open-label trial.", Clinical Neuropharmacology 31(1), 25-33 (2008).

Lerner, et al., "The retinoid X receptor agonist bexarotene relieves positive symptoms of schizophrenia: a 6-week, randomized, double-blind, placebo-controlled multicenter trial", The Journal of Clinical Psychiatry 74(12), 1224-1232 (2013).

Li et al. "Functional Evidence for Retinoid X Receptor (RXR) as a Nonsilent Partner in the Thyroid Hormone Receptor/RXR Heteradimer", Mol. Cell. Biol. 22, 5782-5792 (2002).

Liby, et al. "Synthetic Triterpenoids Prolong Survival in a Transgenic Mouse Model of Pancreatic Cancer", Cancer Prevention Research 3(11), 1427-1434 (2010).

Lindeblad, et al., "Assessment of oral toxicity and safety of 9-cis-UAB30, a potential chemopreventive agent, in rat and dog studies", Drug and Chemical Toxicology 34(3), 300-310 (2011).

Love, et al. "The structural basis for the specificity of retinoid-X receptor-selective agonists: new insights into the role of helix H12", J. Biol. Chem. 277(13), 11385-11391 (2002).

Mangelsdorf, et al., "A direct repeat in the cellular retinal-binding protein type II gene confers differential regulation by RXR and RAR", Cell 66, 555-561 (1991).

Mangelsdorf, et al., "The RXR heterodimers and orphan receptors", Cell 83, 841-850 (1995).

Marshall, "Using *Saccharomyces cerevisiae* to Test the Mutagenicity of Household Compounds: An Open Ended Hypothesis-Driven Teaching Lab", CBE-LSE 6, 307-315 (2007).

McFarland, et al., "Low dose bexarotene treatment rescues dopamine neurons and restores behavioral function in models of Parkinson's disease", ACS Chemical Neuroscience 4, 1430-1438 (2013).

McFarland, "Pimavanserin, a 5-HT2A inverse agonist, reverses psychosis-like behaviors in a rodent model of Parkinson's disease", Behav. Pharmacol. 22, 681-692 (2011).

Michellys, et al., "Design and Synthesis of Novel RXR-Selective Modulators with Improved Pharmacological Profile", Biorg. Met Chem. Lett 13, 4071-4075 (2003).

Michellys, "Design, synthesis and structure-activity relationship of novel RXR-selective modulators", Bioorg. Med. Chem. Lett. 14, 1593-1598 (2004).

Michellys, et al., "Design, synthesis, and structure-activity relationship studies of novel 6,7-locked-[7-(2-alkoxy-3,5-dialkylbenzene)-3-methylocta]-2,4,6-trienoic acids", Journal of Medicinal Chemistry 46, 4087-4103 (2003).

Michellys, et al., "Novel (2E,4E,6Z)-7-(2-alkoxy-3,5-dialkylbenzene)-3-methylocta-2,4,6-trienoic acid retinoid X receptor modulators are active in models of type 2 diabetes", Journal of Medicinal Chemistry 46, 2683-2696 (2003).

Miller, et al., "Initial clinical trial of a selective retinoid X receptor ligand, LGD1069", J. Clin. Oncol. 15, 790-795 (1997).

Morris, et al., "AutoDock4 and AutoDockTools4: Automated Docking with Selective Receptor Flexibility", J. Comput. Chem. 30(16), 2785-2791 (2009).

Mortelmans, "The Amse *Salmonella*/microsome mutagenicity assay", Mutat Res 455, 29-60 (2000).

Muccio, et al., "Conformationally Defined Retinoic Acid Analogues. 4. Potential New Agents for Acute Promyelocytic and Juvenile Myelomonocytic Leukemias", J. Med. Chem. 41, 3766-3769 (1998).

Mukherjee, et al., "Sensitization of diabetic and obese mice to insulin by retinoid X receptor agonists", Nature 386, 407-410 (1997).

Murthy, et al., "LXR/RXR activation enhances basolateral efflux of cholesterol in CaCo-2 cells", J. Lipid Res. 43, 1054-1064 (2002).

Nahoum, et al., "Modulators of the structural dynamics of the retinoid X receptor to reveal receptor function", Proc. Natl. Acad. Sci. 104, 17323-17328 (2007).

Nakatsuka, et al., "RXR antagonism induces G0/G1 cell cycle arrest and ameliorates obesity by up-regulating the p53-p21Cip1 pathway in adipocytes", The Journal of Pathology 226, 784-795 (2012).

O'Boyle, et al., "Open Babel: An open chemical toolbox", J. Cheminf. 3(33), 14 pages (2011).

Ohsawa, et al., "Mechanismof Retinoid X Receptor Partial Agonistic Action of 1-(3,5,5,8,8-Pentamethyl-5,6,7,8-tetrahydro-2-naphthyl)-1H-benzotriazole-5-carboxylic Acid and Structural DevelopmentTo Increase Potency", J. Med. Chem. 56, 1865-1877 (2013).

Ohta, et al., "Diphenylamine-based retinoid antagonists: regulation of RAR and RXR function depending on the N-substituent", Bioorganic & Medicinal Chemistry 19, 2501-2507 (2011).

Ohta, et al., "Potent Retinoid Synergists with a Diphenylamine Skeleton", Biological & Pharmaceutical Bulletin 21(5), 544-546 (1998).

Olefsky, "Nuclear Receptor Minireview Series", J. Biol. Chem. 276(40), 36863-36864 (2001).

Ordentlich, et al., "Identification of the antineoplastic agent 6-mercaptopurine as anactivator of the orphan nuclear hormone receptor Nurr1", J. Biol. Chem. 278(27), 24791-24799 (2003).

Pangborn, et al., "Safe and Convenient Procedure for Solvent Purification", Organometallics 15, 1518-1520 (1996).

Parry, et al., "A Boronated Benzamide as Melanoma-Seeking Agent", Biorg. Med. Chem. Lett. 7(3), 361-364 (1997).

Patent Cooperation Treaty, International Searching Authority, Search Report and Written Opinion for PCT/US16/20285, 9 pages, dated May 20, 2016.

Patent Cooperation Treaty, International Searching Authority, Search Report and Written Opinion for PCT/US2015/17832, 12 pages, dated May 27, 2015.

Patent Cooperation Treaty, International Searching Authority, Search Report and Written Opinion for PCT/US2012/055186, 15 pages, dated May 7, 2013.

Patent Cooperation Treaty, International Searching Authority, Search Report and Written Opinion for PCT/US2015/012066, 11 pages, dated Jun. 25, 2015.

Perlmann, et al., "A novel pathway for vitamin A signaling mediated by RXR heterodimerization with NGFI-B and NURR1", Genes & Dev. 9, 769-782 (1995).

(56) References Cited

OTHER PUBLICATIONS

Perlmann, "Retinoid Metabolism: a balancing act", Nature Genetics 31, 7-8 (2002).
Prince, et al., "Bexarotene capsules and gel for previously treated patients with cutaneous T-cell lymphoma: Results of the Australian patients treated on phase II trials", Australasian Journal of Dermatology 42, 91-97 (2001).
Qing, et al., "A Suzuki Coupling Approach to Trifluoromethyl Derivative of Targretin (LGD 1069).", Bioorganic & Medicinal Chemistry. 17(16), 2117-2120 (1997).
Rigas, "Emerging role of rexinoids in non-small cell lung cancer: focus on bexarotene", Oncologist 10, 22-33 (2005).

* cited by examiner

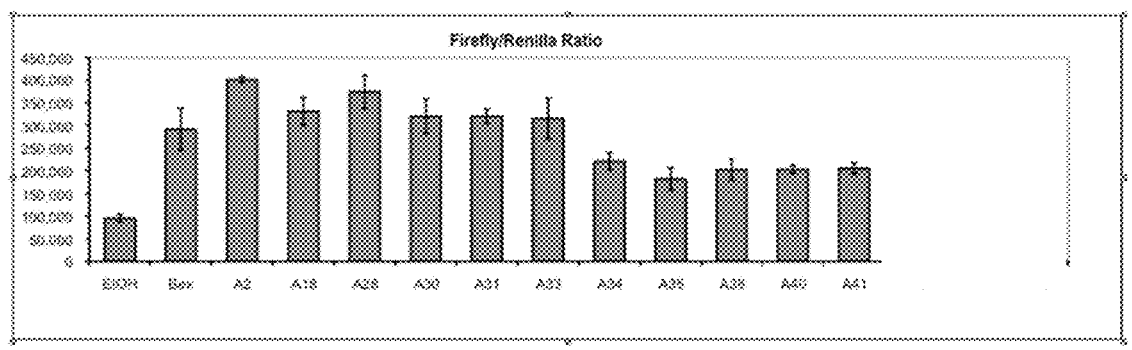
Compounds
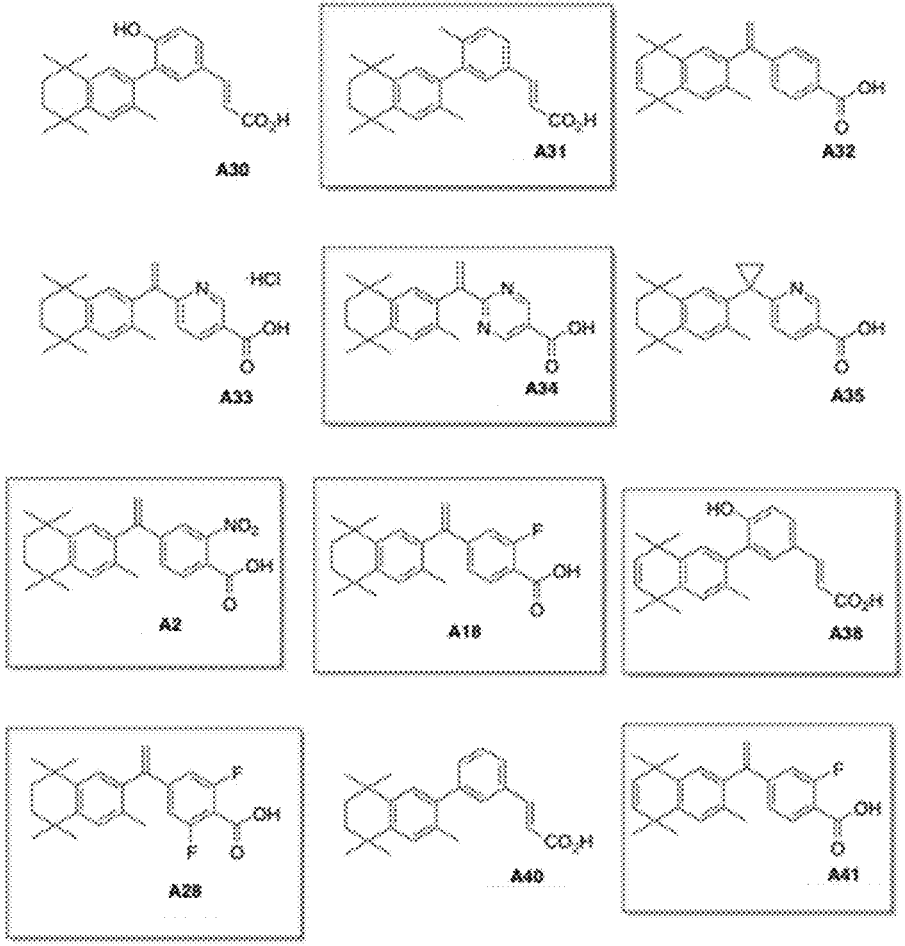

THERAPEUTIC METHODS

RELATED APPLICATION

This application claims the benefit under 35 U.S.C. § 119(e) of U.S. Provisional Application No. 61/928,890, filed Jan. 17, 2014, the entire contents of which is hereby incorporated by reference.

GOVERNMENT FUNDING

This invention was made with government support under R15 CA139364 awarded by the National Institute of Health. The government has certain rights in the invention.

BACKGROUND OF THE INVENTION

The human retinoid X receptors (hRXRs) consist of three identified isoforms (α, β, γ) that function as transcription promoters often in partnership with other members of a larger nuclear receptor (NR) family of transcription regulators including the thyroid receptor (TR), the vitamin D receptor (VDR), the liver X receptor (LXR), the peroxisome proliferator-activated receptor (PPAR), and the retinoic acid receptor (RAR). While 9-cis-retinoic acid (9-cis-RA) and docosahexaenoic acid (DHA) have been shown to bind to hRXRs and promote RXR element (RXRE) regulated transcription (i.e. function as RXR agonists), it is still unclear if RXR has a bona fide endogenous molecular ligand. RXR has been described as the central NR regulator, because it often plays a critical role, either as a permissive or non-permissive partner, in heterodimer complexes that must be formed with the other NRs to regulate their respective response elements.

Recent studies have identified several RXR-selective-binding molecular ligands (rexinoids) that can modulate not only RXRE regulated transcription but also the heterodimer regulated transcription of other NRs. For instance, RXR is a subordinate partner in the RXR-RAR heterodimer, otherwise referred to as a non-permissive heterodimer, since transcription is not promoted in the RAR unliganded (apo-RAR) heterodimer with RXR. Additionally, the RXR-TR heterodimer is non-permissive. In contrast to these non-permissive heterodimers, permissive heterodimers such as RXR-PPAR allow transcription to be promoted in the presence of either RXR or PPAR agonists. The RXR-LXR heterodimer is also permissive. Hence, there is enormous potential for RXR agonists to activate or repress various biological pathways and effect therapeutic results for various conditions that would benefit from activation or repression of a specific pathway.

Six rexinoids described in the literature include Bexarotene (60), CD3254 (61), LGD100268 (62), a pyridyl-bexarotene analog (1), an unsaturated bexarotene analog (2), and the mono-fluorinated bexarotene analog (3).

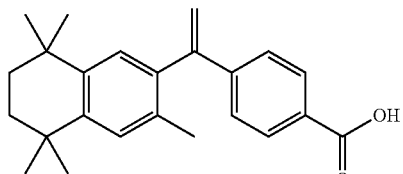

Bexarotene

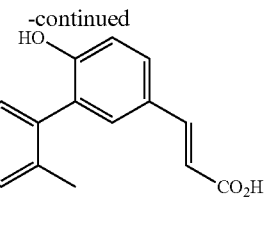

CD 3254

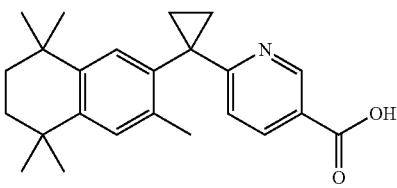

LGD100268

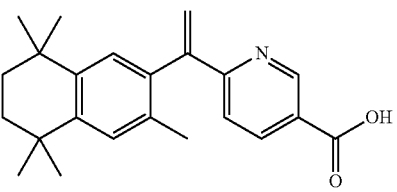

1

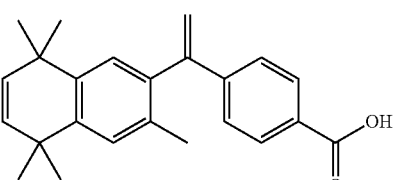

2

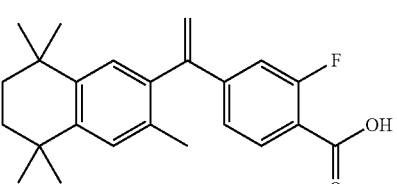

3

Bexarotene has been documented to have an $EC_{50}$ of 33, 24 and 25 nm for the RXR α, β, γ subtypes, respectively, and a $K_d$ of 14, 21, and 29 nm for the RXR α, β, γ subtypes, respectively, in a CV-1 cell line (Boehm, M. F., et al., "Synthesis and Structure-Activity Relationships of Novel Retinoid X Receptor-Selective Retinoids" *J. Med. Chem.* 1994, 37, 2930-2941). CD3254 appears to have an $EC_{50}$ on the order of 10 nm for the hRXRβ isoform (Santin, E. P., et al., "Modulating Retinoid X Receptor with a Series of (E)-3-[4-Hydroxy-3-(3-alkoxy-5,5,8,8-tetramethyl-5,6,7,8-tetrahydronaphthalen-2-yl)phenyl]acrylic Acids and Their 4-Alkoxy Isomers" *J. Med. Chem.* 2009, 52, 3150-3158). LGD100268 and 1 have been documented to have $EC_{50}$s of 4, 3, and 4 nm and 6, 9, and 5 nm for the RXR α, β, γ subtypes, respectively, and $K_d$s of 3, 3, and 3 nm and 22, 61, and 39 nm for the RXR α, β, γ subtypes, respectively, in a CV-1 cell line (Boehm, M. F., et al., "Design and Synthesis of Potent Retinoid X Receptor Selective Ligands That Induce Apoptosis in Leukemia Cells" *J. Med Chem.* 1995, 38, 3146-3155). While the unsaturated-bexarotene analog (2) has been reported, its ability to serve as an RXR agonist has not been published. Finally, the mono-fluorinated bexarotene analog (3) has an $EC_{50}$ of 43 nm and a $K_d$ of 12 nm in hRXR in Caco-2 cells (Wagner, C. E., et al., "Modeling, Synthesis and Biological Evaluation of Potential Retinoid X Receptor (RXR) Selective Agonists: Novel Analogues of 4-[1-(3,5,5,8,8-Pentamethyl-5,6,7,8-tetrahydro-2-naphthyl) ethynyl]benzoic Acid (Bexarotene)" *J. Med. Chem.* 2009, 52, 5950-5966).

Bexarotene has been used to treat cutaneous T cell lymphoma. Bexarotene has also been shown to be useful for treatment of Alzheimer's Disease (AD). However, bexarotene treatment results in untoward side effects, possibly due to its nonspecific nature of binding RXR in several states, including the RXR-RXR homodimer form as well as RXR heterodimer forms.

McFarland, K., et al, *ACS Chem. Neurosci.*, 2013, 4(11), 1430-1438 treated a rat model of Parkinson's disease (PD) with bexarotene and noted marked improvement in the PD symptoms. Specifically the bexarotene restored dopamine cells and natural behavior in the PD model. As importantly, the bexarotene dose that accomplished this was quite low, alleviating some side effects. The researchers demonstrated that these symptoms were alleviated by bexarotene binding to RXR and its heterodimerizing with another nuclear recpetor called Nurr1.

PD is a chronic, debilitating disorder in which the neurons of the central nervous system degenerate over time. Specifically the dopamine secreting cells of the midbrain slowy die off, leaving the patient with a wide range of symptoms due to the lack of dopamine. Early symptoms include shaking, off balance gait, and slowless of muscles. Over time, symptoms worsen and additional symptoms including demetia and/or depression can develop. Treatments include dopamine agonists, given to try to ameliorate the effect of loss of dopamine in the system.

International Patent Application Publication Number WO2011/103321 describes compounds that have RXR agonist activity. Additionally, International Patent Application Publication Number WO2013/040227 describes compounds that have RXR agonist activity.

Currently there is a need for additional chemical agents that are useful for treating PD. In particular, there is a need for agents that have better binding profiles than bexarotene, stimulate gene expression better than bexarotene, or that have better side effect profiles than bexarotene.

SUMMARY OF THE INVENTION

The present invention provides a method for treating a disease or condition associated with dopamine deficiency (e.g. depression, schizophrenia, or Parkinson's disease) in a mammal (e.g. a human) in need of such treatment comprising administering a compound that binds to RXR to the mammal.

The invention also provides a compound that binds to RXR, for the manufacture of a medicament useful for the treatment of a disease or condition associated with dopamine deficiency (e.g. depression, schizophrenia, or Parkinson's disease).

The invention also provides a compound that binds to RXR, for use in the prophylactic or therapeutic treatment of a disease or condition associated with dopamine deficiency (e.g. depression, schizophrenia, or Parkinson's disease).

BRIEF DESCRIPTION OF THE FIGURES

FIG. 1 shows data from Test A for representative compounds.

DETAILED DESCRIPTION

The term "activating", such as used in the phrase "activating RXR", means to promote transcriptional activity.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "6-membered heteroaryl ring" includes rings with at least two carbon atoms and 1, 2, 3, or 4 heteroatoms (e.g. N, O, or S).

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be pyrazinyl, pyridazine, triazine, pyridyl, or pyrimidinyl, or an N-oxide thereof.

Diseases and Condition Associated with Dopamine Deficiency

In one embodiment the disease associated with dopamine deficiency is depression, schizophrenia, or Parkinson's disease; see: Salamone, J. D.; Correa, M. "The Mysterious Motivational Functions of Mesolimbic Dopamine," *Neuron* 2012, 76, 470-485; Lerner, V.; Miodownik, C.; Gibel, A.; Kovalyonok, E.; Shleifer, T.; Goodman, A. B.; Ritsner, M. S. "Bexarotene as add-on to antipsychotic treatment in schizophrenia patients: a pilot open-label trial." *Clin Neuropharmacol* 2008, 31, 25-33; and Lerner, V.; Miodownik, C.; Gibel, A.; Sirota, P.; Bush, I.; Elliot, H.; Benatov, R.; Ritsner, M. S. "The Retinoid X Receptor Agonist Bexarotene Relieves Positive Symptoms of Schizophrenia: A 6-Week, Randomized, Double-Blind, Placebo-Controlled Multicenter Trial" *J Clin Psychiatry* 2013, 74, 1224-1232.

Compounds that Bind to RXR

The ability of a compound to bind to RXR can be determined using assays that are known, for example see: Boehm, M. F.; Zhang, L.; Badea, B. A.; White, S. K.; Mais, D. E.; Berger, E.; Suto, C. M.; Goldman, M. E.; Heyman, R. A. Synthesis and Structure-Activity Relationships of Novel Retinoid X Receptor-Selective Retinoids. *J. Med. Chem.* 1994, 37, 2930-2941; Wagner, C. E.; Jurutka, P. W.; Marshall, P. A.; Groy, T. L.; van der Vaart, A.; Ziller, J. W.; Furmick, J. K.; Graeber, M. E.; Matro, E.; Miguel, B. V.; Tran, I. T.; Kwon, J.; Tedeschi, J. N.; Moosavi, S.; Danishyar, A.; Philp, J. S.; Khamees, R. O.; Jackson, J. N.; Grupe, D. K.; Badshah, S. L.; Hart, J. W. Modeling, Synthesis and Biological Evaluation of Potential Retinoid X Receptor (RXR) Selective Agonists: Novel Analogues of 4-[1-(3,5,5,8,8-Pentamethyl-5,6,7,8-tetrahydro-2-naphthyl)ethynyl]benzoic Acid (Bexarotene). *J. Med. Chem.* 2009, 52, 5950-5966; Furmick, J. K.; Kaneko, I.; Walsh, A. N.; Yang, J.; Bhogal, J. S.; Gray, G. M.; Baso, J. C.; Browder, D. O.; Prentic, J. L. S.; Montano, L. A.; Huynh, C. C.; Marcus, L. M.; Tsosie, D. G.; Kwon, J. S.; Quezada, A.; Reyes, N. M.; Lemming, B.; Saini, P.; van der Vaart, A.; Groy, T. L.; Marshall, P. A.; Jurutka, P. W.; Wagner, C. E. Modeling, Synthesis and Biological Evaluation of Potential Retinoid X Receptor-Selective Agonists: Novel Halogenated Analogues of 4-[1-(3,5,5,8,8-Pentamethyl-5,6,7,8-tetrahydro-2-naphthyl)ethynyl]benzoic Acid (Bexarotene). *ChemMedChem,* 2012, 7, 1551-1566; and Jurutka, P. W.; Kaneko, I.; Yang, J.; Bhogal, J. S.; Swierski, J. C.; Tabacaru, C. R.; Montano, L. A.; Huynh, C. C.; Jama, R. A.; Mahelona, R. D.; Sarnowski, J. T.; Marcus, L. M.; Quezada, A.; Lemming, B.; Tedesco, M. A.; Fischer, A. J.; Mohmed, S. A.; Ziller, J. W.; Ma, N.; Gray, G. M.; van der Vaart, A.; Marshall, P. A.; Wagner, C. E. "Modeling, Synthesis, and Biological Evaluation of Potential Retinoid X Receptor (RXR) Selective Agonists: Novel Analogues of 4-[1-(3,5,5,8,8-Pentamethyl-5,6,7,8-tetrahydro-2-naphthyl)ethynyl]benzoic Acid (Bexarotene) and (E)-3-(3-(1,2,3,4-tetrahydro-1,1,4,4,6-pentamethylnaphthylen-7-yl)-4-hydroxyphenyl)acrylic Acid (CD3254)" *J. Med. Chem.* 2013, 56, 8432-8454.

In one embodiment the compound that binds to RXR activates RXR. The ability of a compound to activate RXR can be determined using assays that are known, for example see WO2013/040227.

In one embodiment the compound that binds to RXR and heterodimerizes with another nuclear recpetor called Nurr1. The ability of a compound to bind to RXR and heterodimerize with Nurr1 can be determined using assays that are known, for example see: Perlmann, T.; Jansson, L. "A novel pathway for vitamin A signaling mediated by RXR heterodimerization with NGFI-B and NURR1." *Genes & Dev.* 1995, 9, 769-782; and Wallén-Mackenzie, Å.; Mata de Urquiza, A.; Petersson, S.; Rodriquez, F. J.; Frilling, S.; and Wagner, J.; Ordentlich, P.; Lengqvist, J.; Heyman, R. A.; Arenas, E.; Perlmann, T. "Nurr1-RXR heterodimers mediate RXR ligand-induced signaling in neuronal cells" *Genes & Dev.* 2003, 17, 3036-3047.

In one embodiment the compound that binds to RXR is a compound described in International Patent Application Publication Number WO2011/10332.

In one embodiment the compound that binds to RXR is a compound described in International Patent Application Publication Number WO2013/040227.

In one embodiment the compound that binds to RXR is a compound of formula XXX:

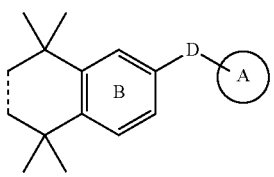

(XXX)

wherein:
the bond represented by --- is a single bond or a double bond;
ring B is optionally substituted with one or more (i.e., 1, 2, or 3) groups independently selected from halo, hydroxy, carboxy, cyano, nitro, $(C_1-C_6)$alkyl, $(C_3-C_6)$cycloalkyl, $(C_2-C_6)$alkenyl, (C2-C6)alkynyl, $(C_1-C_6)$alkoxy, $(C_1-C_6)$alkoxycarbonyl, $(C_1-C_6)$alkanoyloxy, —$B(OH)_2$, and —$SO_3H$, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O);
D is

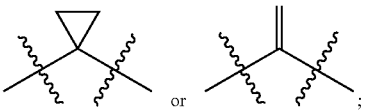

and
ring A is a phenyl ring or a 6-membered heteroaryl ring, which phenyl ring or 6-membered heteroaryl ring is optionally substituted with one or more groups independently selected from halo, hydroxy, carboxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, $(C_1-C_6)$alkanoyloxy, —$B(OH)_2$, and —$SO_3H$, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, carboxy, nitro, cyano, oxo (=O), —$B(OH)_2$, and —$SO_3H$;
or a pharmaceutically acceptable salt thereof;
provided the compound is not bexarotene or a salt thereof.

In one embodiment the compound that binds to RXR is a compound of formula I:

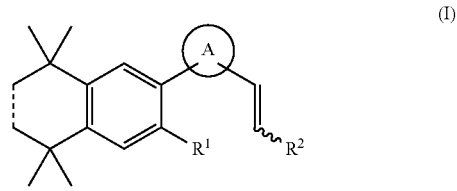

(I)

wherein:
$R^1$ is H, halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O);
the bond represented by --- is a single bond or a double bond;
ring A is a phenyl ring or a 6-membered heteroaryl ring, which phenyl ring or 6-membered heteroaryl ring is optionally substituted with one or more groups independently selected from halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, and oxo (=O); and R² is —COOH, —B(OH)₂, or —SO₃H;
or a pharmaceutically acceptable salt thereof.

In one embodiment ring A for a compound of formula (I) is a phenyl ring substituted with one or more groups independently selected from halo, cyano, nitro, (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, or (C₁-C₆)alkanoyloxy, wherein each (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, and (C₁-C₆)alkanoyloxy, is optionally substituted with one or more groups independently selected from halo, hydroxy, nitro, cyano, and oxo (═O).

In one embodiment ring A for a compound of formula (I) is a 6-membered heteroaryl ring, which is optionally substituted with one or more groups independently selected from halo, hydroxy, cyano, nitro, (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, or (C₁-C₆)alkanoyloxy, wherein each (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, and (C₁-C₆)alkanoyloxy, is optionally substituted with one or more groups independently selected from halo, hydroxy, nitro, cyano, and oxo (═O).

In one embodiment the compound that binds to RXR is a compound of formula II:

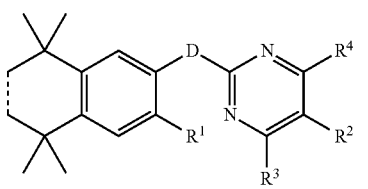

wherein:
R¹ is H, halo, hydroxy, cyano, nitro, (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, or (C₁-C₆)alkanoyloxy, wherein each (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, and (C₁-C₆)alkanoyloxy, is optionally substituted with one or more groups independently selected from halo, hydroxy, nitro, cyano, (C₁-C₆)alkoxy, and oxo (═O);
the bond represented by --- is a single bond or a double bond;
D is

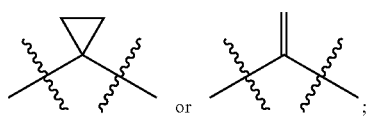

and
at least one of one of R², R³, and R⁴ is —COOH, —B(OH)₂, or —SO₃H; and the remaining R², R³, and R⁴ are each independently selected from H, COOH, —B(OH)₂, —SO₃H, halo, hydroxy, cyano, nitro, (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, or (C₁-C₆)alkanoyloxy, wherein each (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, and (C₁-C₆)alkanoyloxy, is optionally substituted with one or more groups independently selected from halo, hydroxy, nitro, cyano, (C₁-C₆)alkoxy, and oxo (═O);
or a pharmaceutically acceptable salt thereof.

In one embodiment R¹ for a compound of formula (II) is H, halo, hydroxy, cyano, nitro, (C₃-C₆)cycloalkyl, (C₂-C₆)alkenyl, (C₂-C₆)alkynyl, (C₁-C₆)alkoxy, (C₁-C₆)alkoxycarbonyl, or (C₁-C₆)alkanoyloxy, wherein each (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, and (C₁-C₆)alkanoyloxy, is optionally substituted with one or more groups independently selected from halo, hydroxy, nitro, cyano, (C₁-C₆)alkoxy, and oxo (═O).

In one embodiment R¹ for a compound of formula (II) is halo, hydroxy, cyano, nitro, (C₃-C₆)cycloalkyl, (C₂-C₆)alkenyl, (C₂-C₆)alkynyl, (C₁-C₆)alkoxy, (C₁-C₆)alkoxycarbonyl, or (C₁-C₆)alkanoyloxy, wherein each (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, and (C₁-C₆)alkanoyloxy, is optionally substituted with one or more groups independently selected from halo, hydroxy, nitro, cyano, (C₁-C₆)alkoxy, and oxo (═O).

In one embodiment for a compound of formula (II) the bond represented by --- is a single bond.

In one embodiment for a compound of formula (II) the bond represented by --- is a double bond.

In one embodiment for a compound of formula (II) D is

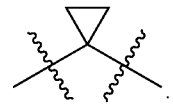

In one embodiment for a compound of formula (II) D is

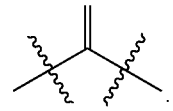 [SMILES: *C(*)=C]

In one embodiment for a compound of formula (II) one of R², R³, and R⁴ is COOH.

In one embodiment for a compound of formula (II) one of R², R³, and R⁴ is —SO₃H.

In one embodiment for a compound of formula (II) at least one of one of R², R³, and R⁴ is —COOH or —SO₃H; and the remaining R², R³, and R⁴ are each independently selected from —COOH, —SO₃H, halo, hydroxy, cyano, nitro, (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, or (C₁-C₆)alkanoyloxy, wherein each (C₁-C₆)alkyl, (C₃-C₆)cycloalkyl, (C₂-C₆)alkenyl, (C₂-C₆)alkynyl, (C₁-C₆)alkoxy, (C₁-C₆)alkoxycarbonyl, and (C₁-C₆)alkanoyloxy, is optionally substituted with one or more groups independently selected from halo, hydroxy, nitro, cyano, (C₁-C₆)alkoxy, and oxo (═O).

In one embodiment the compound that binds to RXR is:

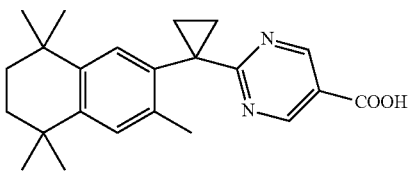 [SMILES: Cc1cc2c(cc1C1(c3ncc(C(=O)O)cn3)CC1)C(C)(C)CCC2(C)C]

or a pharmaceutically acceptable salt thereof.

In one embodiment the compound that binds to RXR is a compound of formula III:

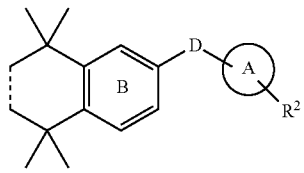

(III)

wherein:
ring B is substituted with at least one group independently selected from R$^a$, halo, hydroxy, cyano, nitro, (C$_2$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, or (C$_1$-C$_6$)alkanoyloxy, wherein each (C$_2$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, and (C$_1$-C$_6$)alkanoyloxy, is optionally substituted with one or more groups independently selected from halo, hydroxy, nitro, cyano, (C$_1$-C$_6$)alkoxy, and oxo (═O);

the bond represented by --- is a single bond or a double bond;

ring A is a phenyl ring or a 6-membered heteroaryl ring, which phenyl ring or 6-membered heteroaryl ring is optionally substituted with one or more groups independently selected from halo, hydroxy, cyano, nitro, (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, or (C$_1$-C$_6$)alkanoyloxy, wherein each (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, and (C$_1$-C$_6$)alkanoyloxy, is optionally substituted with one or more groups independently selected from halo, hydroxy, nitro, cyano, and oxo (═O); R$^2$ is —COOH, —B(OH)$_2$, or —SO$_3$H;

D is

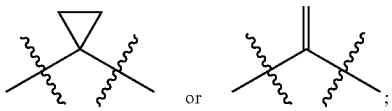

and
R$^a$ is methyl that is substituted with hydroxy, nitro, cyano, (C$_1$-C$_6$)alkoxy, or oxo (═O), or methyl that is substituted with one or more halo;
or a pharmaceutically acceptable salt thereof.

In one embodiment for a compound of formula (III) the bond represented by --- is a single bond.

In one embodiment for a compound of formula (III) the bond represented by --- is a double bond.

In one embodiment for a compound of formula (III) ring B is substituted with at least one group independently selected from R$^a$, fluoro, chloro, iodo, hydroxy, cyano, nitro, (C$_2$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, or (C$_1$-C$_6$)alkanoyloxy, wherein each (C$_2$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, and (C$_1$-C$_6$)alkanoyloxy, is optionally substituted with one or more groups independently selected from halo, hydroxy, nitro, cyano, (C$_1$-C$_6$)alkoxy, and oxo (═O).

In one embodiment for a compound of formula (III) ring B is substituted with at least one group independently selected from R$^a$, hydroxy, cyano, nitro, (C$_2$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, or (C$_1$-C$_6$)alkanoyloxy, wherein each (C$_2$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, and (C$_1$-C$_6$)alkanoyloxy, is optionally substituted with one or more groups independently selected from halo, hydroxy, nitro, cyano, (C$_1$-C$_6$)alkoxy, and oxo (═O).

In one embodiment for a compound of formula (III) D is

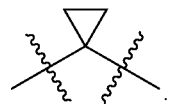

In one embodiment for a compound of formula (III) D is

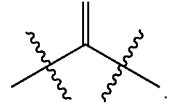 [SMILES: *C(*)=C]

In one embodiment for a compound of formula (HI) ring A is a phenyl ring substituted with one or more groups independently selected from halo, cyano, nitro, (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, or (C$_1$-C$_6$)alkanoyloxy, wherein each (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, and (C$_1$-C$_6$)alkanoyloxy, is optionally substituted with one or more groups independently selected from halo, hydroxy, nitro, cyano, and oxo (═O).

In one embodiment for a compound of formula (III) ring A is a 6-membered heteroaryl ring, which is optionally substituted with one or more groups independently selected from halo, hydroxy, cyano, nitro, (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, or (C$_1$-C$_6$)alkanoyloxy, wherein each (C$_1$-C$_6$)alkyl, (C$_3$-C$_6$)cycloalkyl, (C$_2$-C$_6$)alkenyl, (C$_2$-C$_6$)alkynyl, (C$_1$-C$_6$)alkoxy, (C$_1$-C$_6$)alkoxycarbonyl, and (C$_1$-C$_6$)alkanoyloxy, is optionally substituted with one or more groups independently selected from halo, hydroxy, nitro, cyano, and oxo (═O).

In one embodiment for a compound of formula (III) R$^2$ is —COOH.

In one embodiment for a compound of formula (III) R$^2$ is —SO$_3$H.

In one embodiment the compound that binds to RXR is a compound of formula IV:

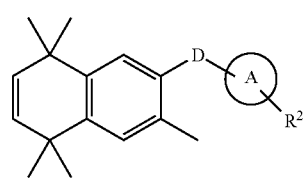

(IV)

wherein:

ring A is a phenyl ring or a 6-membered heteroaryl ring, which phenyl ring or 6-membered heteroaryl ring is optionally substituted with one or more groups independently selected from halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, and oxo (=O);

$R^2$ is —COOH, —B(OH)$_2$, or —SO$_3$H; and

D is

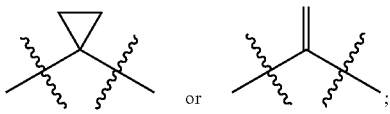

or a pharmaceutically acceptable salt thereof.

In one embodiment for a compound of formula (IV) ring A is a phenyl ring substituted with one or more groups independently selected from halo, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, and oxo (=O).

In one embodiment for a compound of formula (IV) ring A is a 6-membered heteroaryl ring, which is optionally substituted with one or more groups independently selected from halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, and oxo (=O).

In one embodiment for a compound of formula (IV) D is

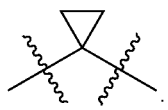 [SMILES: *C1(*)CC1]

In one embodiment for a compound of formula (IV) D is

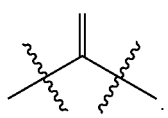 [SMILES: *C(*)=C]

In one embodiment for a compound of formula (IV) $R^2$ is —COOH.

In one embodiment for a compound of formula (IV) $R^2$ is —SO$_3$H.

In one embodiment the compound that binds to RXR is selected from:
2-(1-(1,2,3,4-tetrahydro-1,1,4,4,6-pentamethylnaphthalen-7-yl)vinyl)pyrimidine-5-carboxylic acid,
2-[1-(3,5,5,8,8-pentamethyl-5,6,7,8-tetrahydronaphthalen-2-yl)cyclopropyl]pyrimidine-2-carboxylic acid,
(E)-3-(3-(1,2,3,4-tetrahydro-1,1,4,4,6-pentamethylnaphthalen-7-yl)-4-methylphenyl)acrylic acid,
(2E)-3-(3-(1,4-dihydro-1,1,4,4,6-pentamethylnaphthalen-7-yl)-4-methylphenyl)acrylic acid,
(2E)-3-(3-(1,4-dihydro-1,1,4,4,6-pentamethylnaphthalen-7-yl)-4-hydroxyphenyl)acrylic acid,
(E)-3-(4-(trifluoromethyl)-3-(1,2,3,4-tetrahydro-1,1,4,4,6-pentamethylnaphthalen-7-yl)phenyl)acrylic acid,
2-fluoro-4-(1-(1,4-dihydro-1,1,4,4,6-pentamethylnaphthalen-7-yl)vinyl)benzoic acid,
(E)-3-(5-(1,2,3,4-tetrahydro-1,1,4,4,6-pentamethylnaphthalen-7-yl)-6-methylpyridin-3-yl)acrylic acid, and
(E)-3-(4-(1,2,3,4-tetrahydro-1,1,4,4,6-pentamethylnaphthalen-7-yl)-5-methylpyridin-2-yl)acrylic acid,
and salts thereof.

In one embodiment the compound of formula XXX is a compound having the formula:

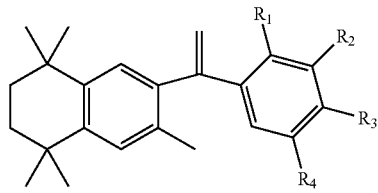

wherein $R_1$, $R_2$, $R_3$ and $R_4$ are each independently selected from the group consisting of hydrogen, hydroxy, $C_{1-6}$alkyl, $C_{1-6}$alkoxy, thiol, halogen, —CO$_2$H, —CO$_2$C$_{1-6}$alkyl, —SO$_3$H, —NH$_2$, —NH($C_{1-6}$alkyl), and —N($C_{1-6}$alkyl)$_2$, or a pharmaceutically acceptable salt thereof.

In one embodiment at least one of $R_1$, $R_2$, $R_3$ and $R_4$ is CO$_2$H.

In one embodiment $R_3$ is —CO$_2$H.

In one embodiment $R_1$ is a halogen.

In one embodiment $R_2$ and $R_4$ are hydrogen.

In one embodiment $R_1$ is a halogen and $R_4$ is a halogen.

In one embodiment said halogen is selected from the group consisting of F, Br, Cl, and I, and said halogen is the same as the halogen at $R_1$ or different from the halogen at $R_1$.

In one embodiment $R_2$ is a halogen.

In one embodiment said halogen is selected from the group consisting of F, Br, Cl, and I, and said halogen is the same as the halogen at $R_1$ and/or R4 or different from the halogen at $R_1$ and/or $R_4$.

In one embodiment $R_1$ is H, $R_2$ is F, $R_3$ is —COOH, and $R_4$ is F.

In one embodiment $R_4$ is a halogen.

In one embodiment the compound of formula XXX is a compound having the formula:

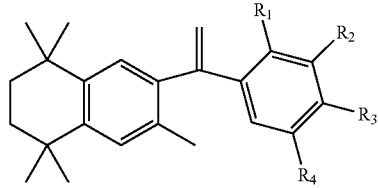

having the following substituents at each of positions $R_1$, $R_2$, $R_3$, R4:

| Compound # | $R_1$ | $R_2$ | $R_3$ | $R_4$ |
|---|---|---|---|---|
| 2 | $CO_2H$ | H | H | $CO_2H$ |
| 3 | H | $NO_2$ | $CO_2H$ | H |
| 4 | H | $CO_2H$ | $CO_2H$ | H |
| 5 | H | $CO_2H$ | $CO_2H$ | $CO_2H$ |
| 6 | F | F | $CO_2H$ | H |
| 7 | H | F | $CO_2H$ | F |

In one embodiment the compound of formula XXX is a compound having the formula:

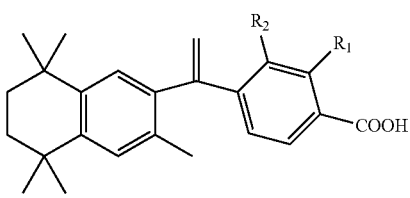

wherein $R_2$ and $R_1$ are each independently selected from the group consisting of hydrogen, hydroxy, $C_{1-6}$alkyl, $C_{1-6}$alkoxy, thiol, halogen, —$CO_2H$, —$CO_2C_{1-6}$alkyl, —$SO_3H$, —$NH_2$, —$NH(C_{1-6}$alkyl), and —$N(C_{1-6}$alkyl$)_2$, or a pharmaceutically acceptable salt thereof.

In one embodiment the compound of formula XXX is a compound having the formula:

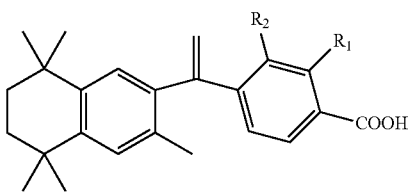

wherein $R_2$ and $R_1$ are defined as:

| Compound # | $R_1$ | $R_2$ |
|---|---|---|
| 8 | H | F |
| 9 | F | H |
| 10 | Cl | H |
| 11 | Br | H |
| 12 | I | H |
| 10a | H | Cl |
| 11a | H | Br |
| 12a | H | I |
| 10b | Cl | Cl |
| 11b | Br | Br |
| 12b | I | I |

In one embodiment the compound of formula XXX is a compound having the formula XIII:

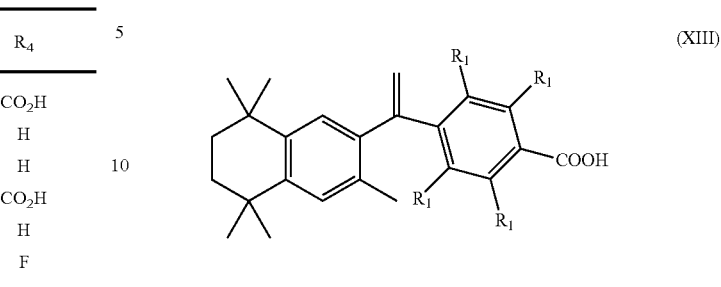

in which each of the $R_1$ moieties is a halogen.

In one embodiment the compound of formula XXX is a compound having Formula 4:

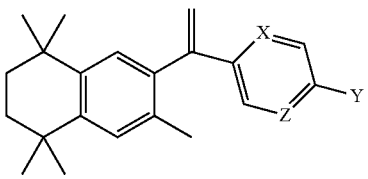

in which X and Z are each independently selected from —CH—, —N—, —S—, or —O—. In specific preferred embodiments, each of X and Z are CH, in other embodiments, each of X and Z are N, in still other embodiments Z is either CH or N and X is either CH or N provided that when Z is CH X is N and when Z is N, X is CH. In the foregoing exemplary embodiments Y is either —B(OH)$_2$ or $CO_2H$.

In one embodiment the compound of formula XXX is a compound having Formula 4:

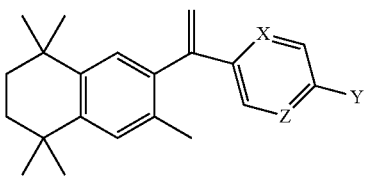

in which X and Z are N; and Y is either —B(OH)$_2$ or $CO_2H$; or a pharmaceutically acceptable salt thereof.

In one embodiment the compound of formula XXX is a compound having Formula 4:

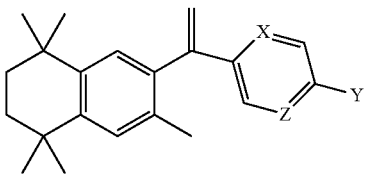

in which Z is CH and X is N; or Z is N and X is CH; and Y is either —B(OH)$_2$ or $CO_2H$; or a pharmaceutically acceptable salt thereof.

In one embodiment Y is $CO_2H$.

In one embodiment the compound of formula XXX is a compound having Formula 5:
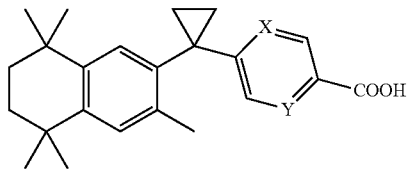
in which X is CH and Y is N or X is N and Y is CH; or a pharmaceutically acceptable salt thereof.
In one embodiment the compound that binds to RXR is a compound selected from:
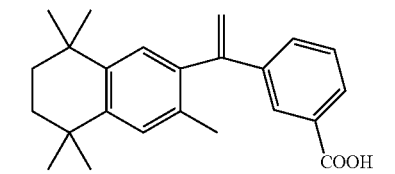
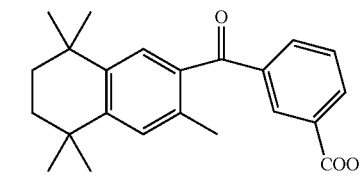
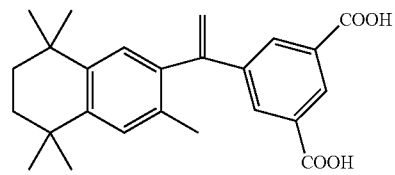
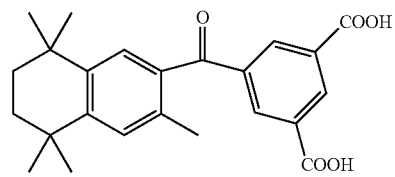
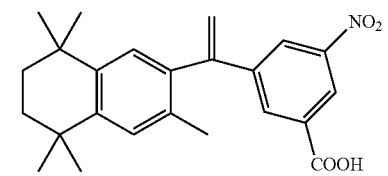
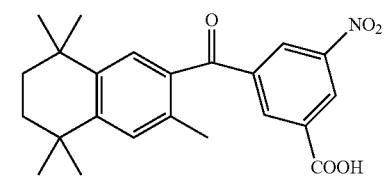
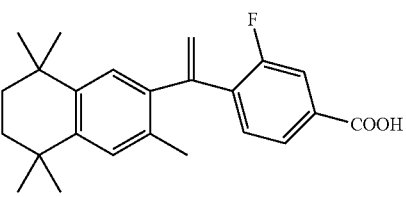
-continued
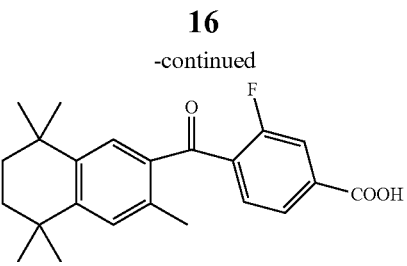
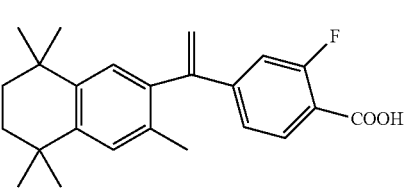
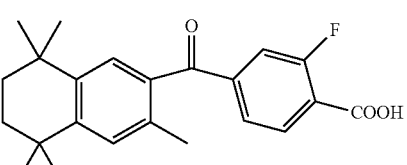
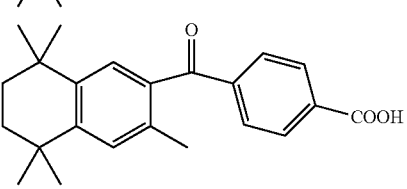
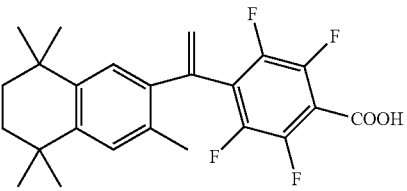
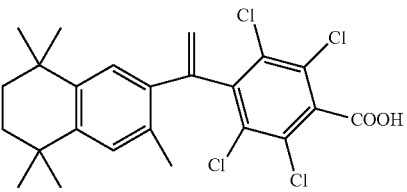
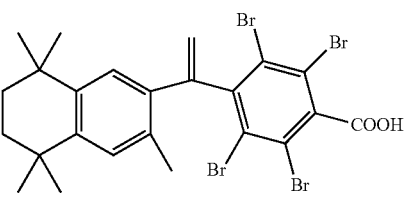
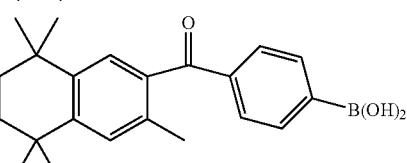
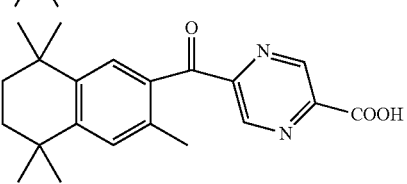

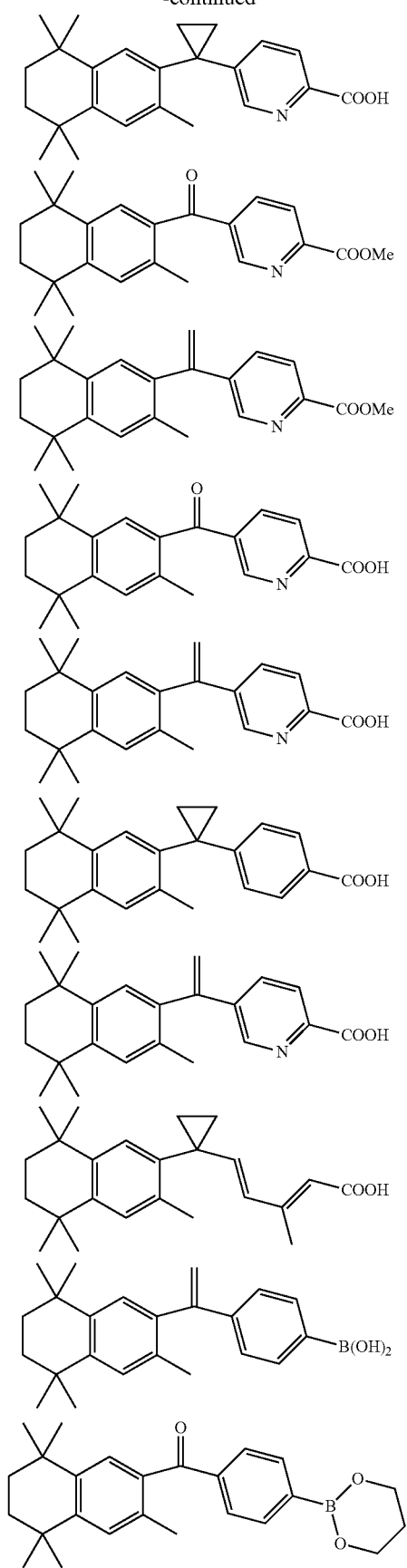
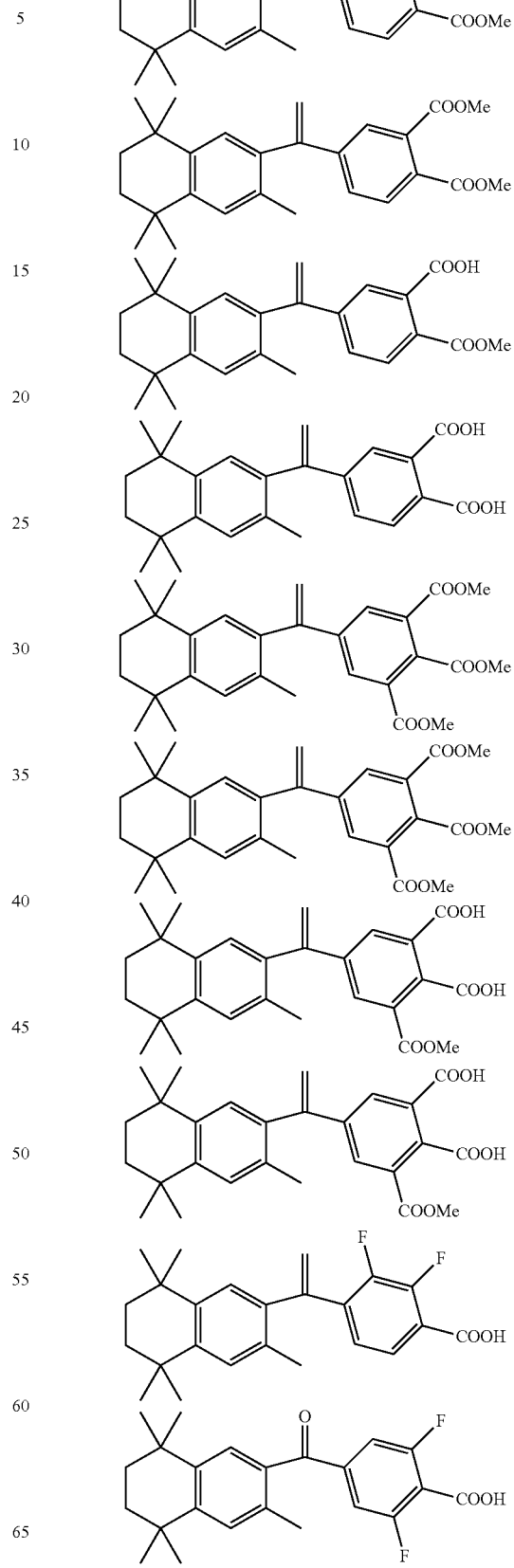

-continued

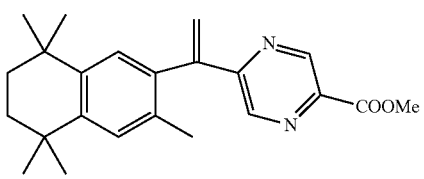

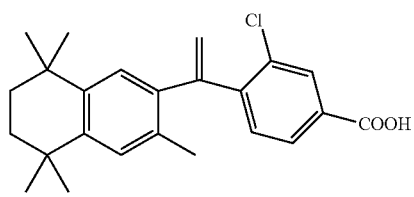

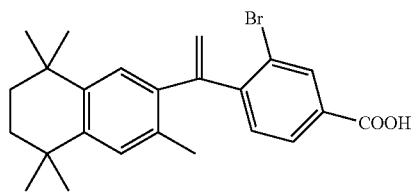

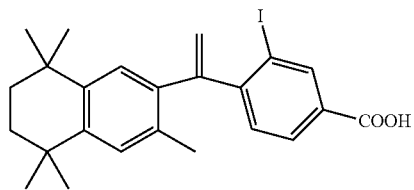

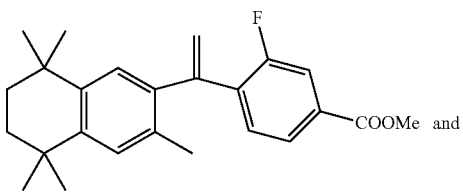

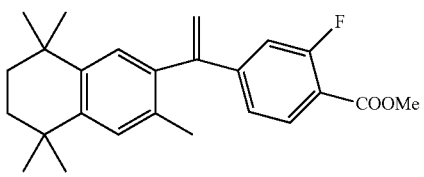 [SMILES: C=C(c1ccc(C(=O)OC)c(F)c1)c1cc2c(cc1C)C(C)(C)CCC2(C)C]

and salts thereof.

In one embodiment the compound that binds to RXR is a compound selected from:

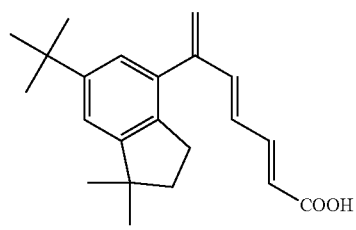

-continued

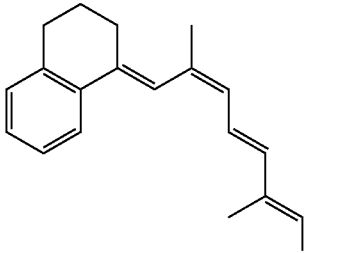

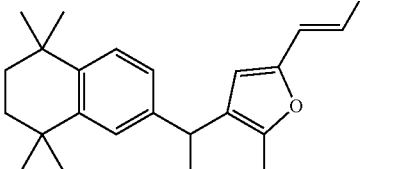

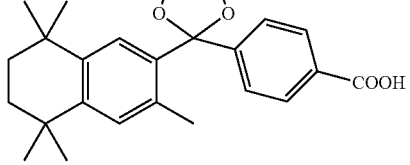

and salts thereof.

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949. Compounds that are non-toxic and non-mutagenic at typical dose levels will have useful doses. (Mortelmans, K.; Zeiger, E. "The Ames *Salmonella*/microsome mutagenicity assay." Mutat. Res. 2000, 455, 29-60.)

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form. In certain embodiments, the dose is about 300 mg/m$^2$/day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds can also be administered in combination with other therapeutic agents. In certain embodiments, compounds of the invention can be administered in combination with agents that are useful for the treatment of diseases associated with dopamine deficiency. For example, the compounds can be administered (and/or formulated) with clozapine, olanzapine, haloperidol, risperidone, perphenazine, quetiapine, or chlorpromazine.

Compounds that bind to RXR, including the specific compounds described herein, can be prepared using procedures that are known. Such procedures include those described in International Patent Application Publication Number WO2011/103321 and in International Patent Application Publication Number WO2013/040227.

Test A

The ability of a compound to activate Nurr1 can be evaluated using assays that are known. For example, representative compounds were evaluated using an assay similar to that described by Wallen-Mackenzie, A. et al., *Genes Dev* 2003, 17, 3036-3047. Data is provided in FIG. 1 for the compounds shown therein.

All publications, patents, and patent documents (including International Patent Application Publication Number WO2011/103321 and in International Patent Application Publication Number WO2013/040227) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating a disease or condition associated with dopamine deficiency in a mammal in need of such treatment comprising administering a compound that binds to RXR to the mammal, provided the compound that binds to RXR is not bexarotene, wherein the compound that binds to RXR is a compound of formula XXX:

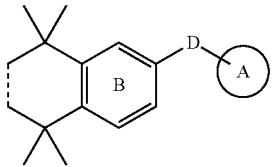

(XXX)

wherein:
the bond represented by --- is a single bond or a double bond;
ring B is optionally substituted with one or more (i.e., 1, 2, or 3) groups independently selected from halo, hydroxy, carboxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, $(C_1-C_6)$alkanoyloxy, —B(OH)$_2$, and —SO$_3$H, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O);
D is

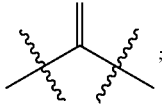

and
ring A is a phenyl ring or a 6-membered heteroaryl ring other than pyridyl, which phenyl ring or 6-membered heteroaryl ring other than pyridyl is optionally substituted with one or more groups independently selected from halo, hydroxy, carboxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, $(C_1-C_6)$alkanoyloxy, —B(OH)$_2$, and —SO$_3$H, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, carboxy, nitro, cyano, oxo (=O), —B(OH)$_2$, and —SO$_3$H;
or a pharmaceutically acceptable salt thereof, wherein the disease or condition associated with dopamine deficiency is Parkinson's disease.

2. The method of claim 1 wherein the compound that binds to RXR is a compound of formula II:

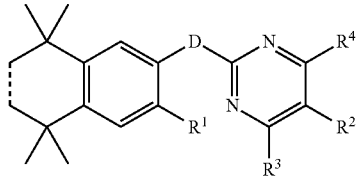

(II)

wherein:
$R^1$ is H, halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O);
the bond represented by --- is a single bond or a double bond;
D is

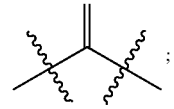

and
at least one of one of $R^2$, $R^3$, and $R^4$ is —COOH, —B(OH)$_2$, or —SO$_3$H; and the remaining $R^2$, $R^3$, and $R^4$ are each independently selected from H, —COOH, —B(OH)$_2$, —SO$_3$H, halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O);
or a pharmaceutically acceptable salt thereof.

3. The method of claim 2 wherein $R^1$ is H, halo, hydroxy, cyano, nitro, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O).

4. The method of claim 2 wherein $R^1$ is halo, hydroxy, cyano, nitro, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, or $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O).

5. The method of claim 2 wherein the bond represented by --- is a single bond.

6. The method of claim 2 wherein the bond represented by --- is a double bond.

7. The method of claim 2 wherein one of $R^2$, $R^3$, and $R^4$ is COOH.

8. The method of claim 2 wherein one of $R^2$, $R^3$, and $R^4$ is —$SO_3H$.

9. The method of claim 2 wherein at least one of one of $R^2$, $R^3$, and $R^4$ is —COOH or —$SO_3H$; and the remaining $R^2$, $R^3$, and $R^4$ are each independently selected from —COOH, —$SO_3H$, halo, hydroxy, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, $(C_1-C_6)$alkoxy, and oxo (=O).

10. The method of claim 1 wherein the compound has the formula:

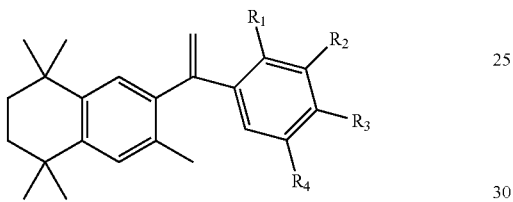

wherein $R_1$, $R_2$, $R_3$ and $R_4$ are each independently selected from the group consisting of hydrogen, hydroxy, $C_{1-6}$alkyl, $C_{1-6}$alkoxy, thiol, halogen, —$CO_2H$, —$CO_2(C_{1-6}alkyl)$, —$SO_3H$, —$NH_2$, —NH$(C_{1-6}alkyl)$, and —N$(C_{1-6}alkyl)_2$, or a pharmaceutically acceptable salt thereof.

11. The method of claim 10 wherein the compound is a compound having the formula:

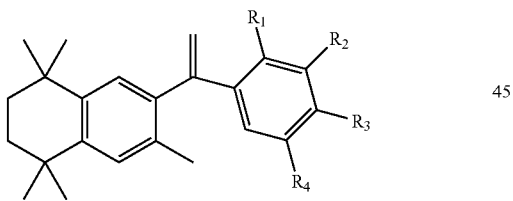

having the following substituents at each of positions $R_1$, $R_2$, $R_3$, $R_4$:

| Compound # | $R_1$ | $R_2$ | $R_3$ | $R_4$ |
|---|---|---|---|---|
| 2 | $CO_2H$ | H | H | $CO_2H$ |
| 3 | H | $NO_2$ | $CO_2H$ | H |
| 4 | H | $CO_2H$ | $CO_2H$ | H |
| 5 | H | $CO_2H$ | $CO_2H$ | $CO_2H$ |
| 6 | F | F | $CO_2H$ | H |
| 7 | H | F | $CO_2H$ | F |

12. A method for treating a disease or condition associated with dopamine deficiency in a mammal in need of such treatment comprising administering a compound that binds to RXR to the mammal, wherein the compound that binds to RXR is a compound selected from:

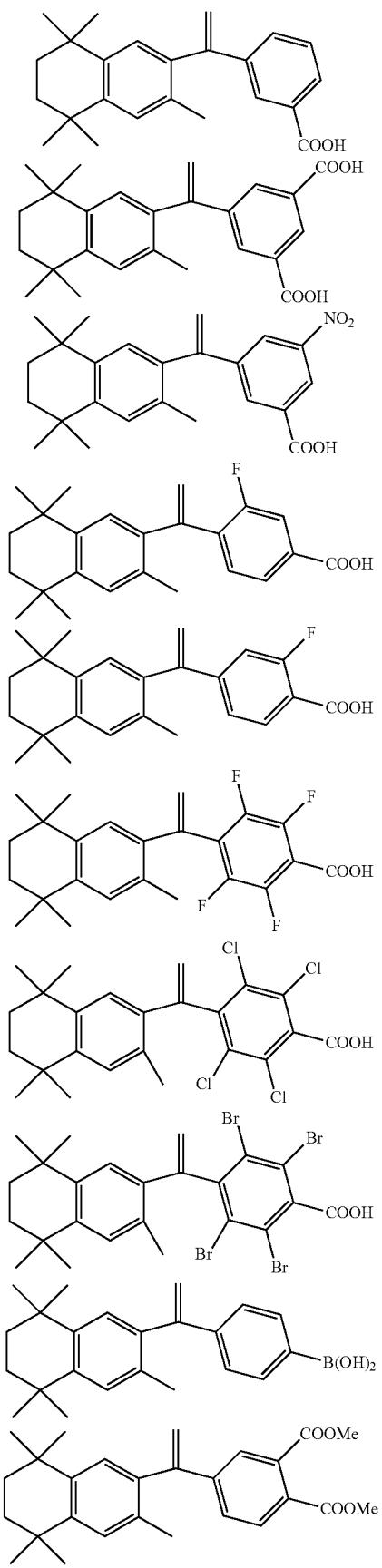

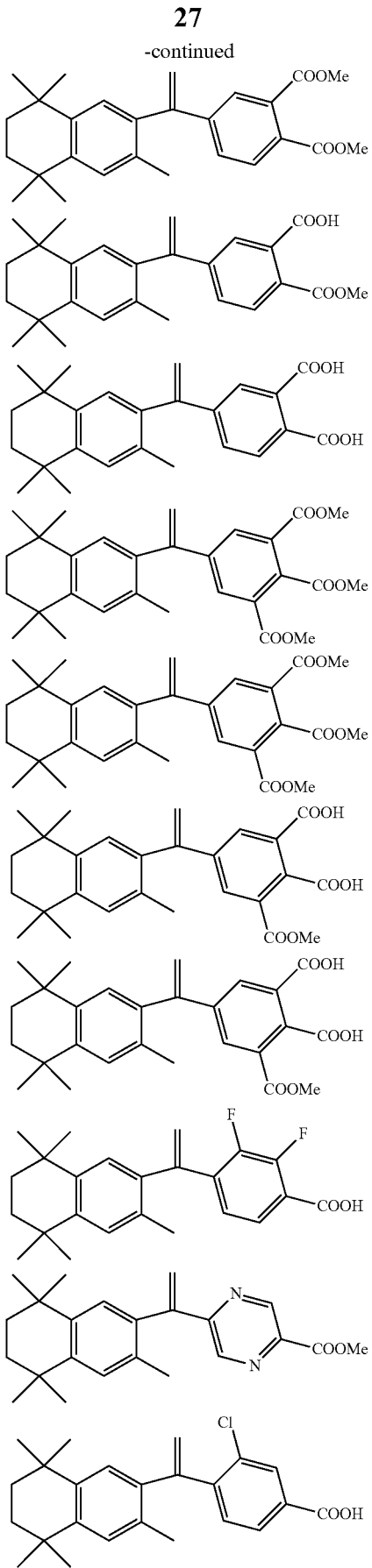

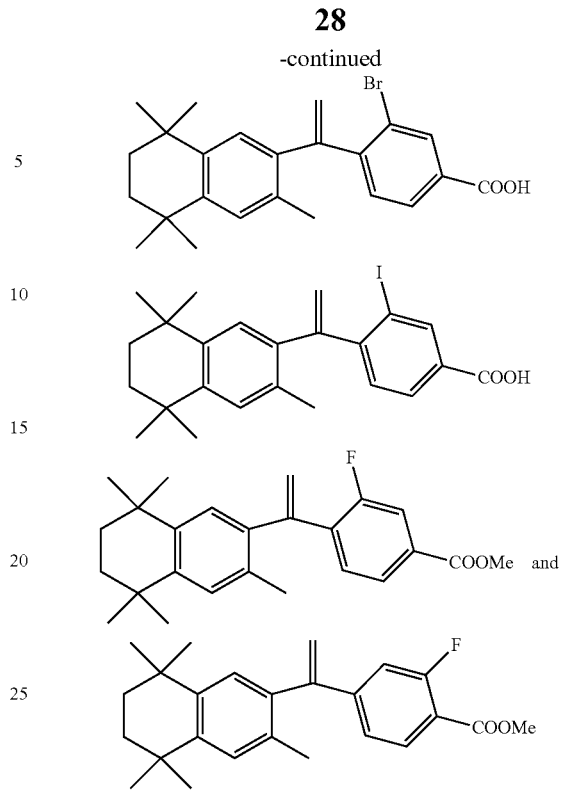

or a pharmaceutically acceptable salt thereof, wherein the disease or condition associated with dopamine deficiency is Parkinson's disease.

13. A method for treating a disease or condition associated with dopamine deficiency in a mammal in need of such treatment comprising administering a compound that binds to RXR to the mammal, provided the compound that binds to RXR is not bexarotene, wherein the compound that binds to RXR is a compound of formula IV:

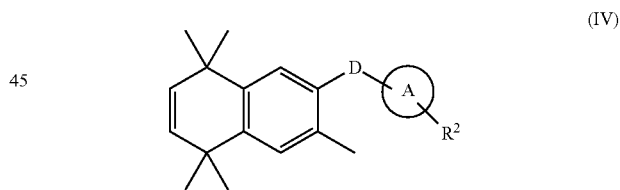

(IV)

wherein:
ring A is a phenyl ring or a 6-membered heteroaryl ring other than pyridyl, which phenyl ring or 6-membered heteroaryl ring other than pyridyl is optionally substituted with one or more groups independently selected from halo, hydroxy, cyano, nitro, $(C_1-C_6)$ alkyl, $(C_3-C_6)$cycloalkyl, $(C_2-C_6)$alkenyl, $(C_2-C_6)$ alkynyl, $(C_1-C_6)$alkoxy, $(C_1-C_6)$alkoxycarbonyl, and $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$ alkanoyloxy, is optionally substituted with one or more groups independently selected from halo, hydroxy, nitro, cyano, and oxo (=O);

$R^2$ is —COOH, —B(OH)$_2$, or —SO$_3$H; and

D is

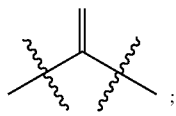

;

or a pharmaceutically acceptable salt thereof, wherein the disease or condition associated with dopamine deficiency is Parkinson's disease.

14. The method of claim 13 wherein ring A is a phenyl ring substituted with one or more groups independently selected from halo, cyano, nitro, $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, wherein each $(C_1-C_6)$alkyl, $(C_3-C_6)$cycloalkyl, $(C_2-C_6)$alkenyl, $(C_2-C_6)$alkynyl, $(C_1-C_6)$alkoxy, $(C_1-C_6)$alkoxycarbonyl, and $(C_1-C_6)$alkanoyloxy, is optionally substituted with one or more groups independently selected from halo, hydroxy, nitro, cyano, and oxo (=O).

15. The method of claim 13 wherein $R^2$ is —COOH.

16. A method for treating a disease or condition associated with dopamine deficiency in a mammal in need of such treatment comprising administering a compound that binds to RXR to the mammal, wherein the compound that binds to RXR is compound

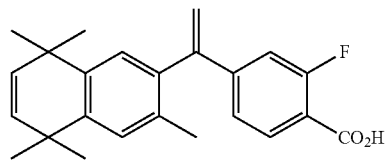 [SMILES: C=C(c1ccc(C(=O)O)c(F)c1)c1cc2c(cc1C)C(C)(C)C=CC2(C)C]

or a pharmaceutically acceptable salt thereof, wherein the disease or condition associated with dopamine deficiency is Parkinson's disease.

* * * * *